United States Patent [19]

Devaux et al.

[11] Patent Number: 6,114,586
[45] Date of Patent: Sep. 5, 2000

[54] PRODUCTION OF STABILIZED AND DEODORIZED ORGANIC POLYSULPHIDES

[75] Inventors: Jean-François Devaux, Jurançon; Georges Fremy, Os-Marsillon; Yves Labat, Pau, all of France

[73] Assignee: Elf Atochem S.A., France

[21] Appl. No.: 09/235,272

[22] Filed: Jan. 22, 1999

[30] Foreign Application Priority Data

Feb. 3, 1998 [FR] France .................................. 98 01225

[51] Int. Cl.⁷ .................................................. C07C 321/12
[52] U.S. Cl. .................................................. 568/21; 568/25

[58] Field of Search .......................................... 568/21, 25

[56] References Cited

U.S. PATENT DOCUMENTS 4,355,183  10/1982  Nash .......................................... 568/19
5,559,271   9/1996  Shaw .......................................... 568/21

*Primary Examiner*—Gary Geist
*Assistant Examiner*—Jean F. Vollano

[57] ABSTRACT

A process for stabilizing and deodorizing a raw organic polysulfide by treating it with an alkylene carbonate in the presence of a basic catalyst and, optionally, a sulfur donor.

28 Claims, No Drawings

PRODUCTION OF STABILIZED AND DEODORIZED ORGANIC POLYSULPHIDES

FIELD OF THE INVENTION

The present invention concerns the field of organic polysulphides, and relates more particularly to the manufacture of stabilized and deodorized organic polysulphides.

BACKGROUND OF THE INVENTION

Organic polysulphides, which can be represented by the general formula $RS_nR'$ in which n is an integer ranging from 2 to 15 and R and R' are optionally substituted hydrocarbyl radicals, are used in numerous applications such as, for example, presulphurization of hydrorefining catalysts and addition to elastomers. They are also excellent extreme-pressure and anti-wear additives for lubricants, and are therefore involved in the composition of lubricating formulations for gearboxes and for machining metals. Most applications require a polysulphide which is odorless, precipitate-free, clear and stable in the long-term.

However, organic polysulphides are generally prepared by reacting a mercaptan with elementary sulphur in the presence of a basic catalyst; they may also be prepared from an olefin, sulphur and/or hydrogen sulphide, optionally in the presence of a basic catalyst. Products prepared in this way contain or release hydrogen sulphide and/or mercaptans, which are difficult to remove.

Hydrogen sulphide is toxic and, together with mercaptans, causes unpleasant odours. Furthermore in the possible presence of catalytic residues, the residual mercaptan and hydrogen sulphide make the finished product unstable, leading to some degree of turbidity or the appearance of precipitates in the course of time.

In order to deodorize and stabilize organic polysulphides, it is essential to remove the mercaptan and hydrogen sulphide residues by suitable treatment. Various processes for solving this problem have already been described:

washing the raw polysulphide with an acid and/or babe solution (U.S. Pat. No. 5,155,275);

washing the raw polysulphide with an oxidizing solution in the presence of a catalytic amount of base (U.S. Pat. No. 5,206,439);

washing the raw polysulphide with an alcoholic or aqueous solution of a metal salt (U.S. Pat. No. 5,403,961);

treating the raw polysulphide with an acid and subsequent distillation (U.S. Pat. No. 5,530,163);

treating the raw polysulphide with an alkene oxide in the presence of a catalytic amount of base (Patents JP 58-140063 and U.S. Pat. No. 5,218,147).

These processes are not entirely satisfactory. The washing processes require the addition of solvents or aqueous solutions which are difficult to separate from the polysulphide at the end of the treatment, unless time-consuming and expensive separation means are employed. The process involving final distillation is expensive in terms of energy and is applicable only to light polysulphides. Alkene oxides are toxic and carcinogenic.

Some methods do not make it possible, in a single treatment, to reduce the residual mercaptan sulphur level to a level which is low enough to stabilize the polysulphide; the need to carry out several successive treatments makes these time-consuming and expensive methods.

DESCRIPTION OF THE INVENTION

A process has now been found for stabilizing polysulphides and reducing the residual mercaptan level, which is fast, uses not very toxic reactants and does not require the use of a solvent or phase mixture, or distillation.

The process according to the invention for preparing a stabilized and deodorized organic polysulphide consists in treating a raw organic polysulphide with an alkylene carbonate in the presence of a basic catalyst and, optionally, a sulphur donor.

The present invention will now be described in detail.

a—Definition of the Polysulphide of the Invention

The organic polysulphide of the present invention satisfies the general formula $RS_nR'$ in which n is a number ranging from 2 to 15 and the symbols R and R', which may be identical or different, generally denote hydrocarbyl radicals having 1 to 20 carbon atoms and possibly having one or more unsaturations. These radicals are most often alkyl, cycloalkyl or aryl radicals; some of the hydrogen atoms of alkyl or cycloalkyl radicals may be replaced by formyl or acyl (—COR"), carboxyl or carboxylic ester (—COOR"), carbonitrile, azomethine (—CR"=NR'"), carboxamide (—CONR"R'"), nitro, hydroxyl, alkoxy, amino (—NR"R'"), —SiR""$_3$ functional groups, or by aryl or cycloalkyl groups, the symbols R" and R'", which may be identical or different, each representing a hydrogen atom or an alkyl radical, and the three substituents R"", which may be identical or different, being alkyl or alkoxy radicals. Preferably, R and R' are alkyl radicals, which may or may not be branched, having 4 to 12 carbon atoms and n is a number ranging from 3 to 6.

The organic polysulphide may also be the product of the sulphurization of an olefin, a polyolefin, a polyunsaturated olefin, a fatty oil, a fatty ester or a fatty acid. Sulphurized olefins comprise products made by sulphurizing an olefin (for example isobutylene) or a polyolefin (for example diisobutylene) with sulphur, sulphur chloride, sulphur dichloride or hydrogen sulphide, or a combination of these products, optionally in the presence of a basic catalyst. The oils which may be sulphurized are natural or synthetic oils comprising mineral oils, lard oils, carboxylic esters derived from aliphatic alcohols and fatty acids or aliphatic carboxylic acids, and unsaturated esters or glycerides. The fatty acids generally contain from 8 to 30 carbon atoms and are, for example, palmitoleic, oleic, ricinoleic, linoleic, oleostearic acid, etc. The sulphurized fatty acid esters may also be prepared from mixtures of fatty acid esters such as those obtained from animal fats or vegetable oils.

b—Definition of the Raw Polysulphide and Mode of Preparation (Processes Which are Already Known)

The raw organic polysulphide of the present invention may be prepared by a wide variety of processes. One preparation method known in the prior art consists in reacting one or more mercaptans with elementary sulphur in the presence of a basic catalyst according to the following reaction:

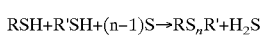

Processes for preparing organic polysulphides according to this method are described, for example, in U.S. Pat. Nos. 2,237,625, 3,022,351, 3,038,013, 3,392,201, 4,564,709, 5,206,439, 5,530,163, FR 1 381 625, FR 1 553 249, FR 2 607 496, FR 2 635 775, EP 25944, EP 337837, WO 97/21649 and WO 97/21673.

The raw organic polysulphide may also be produced by sulphurizing an olefin, polyolefin, fatty oil, fatty ester or fatty acid, using the processes described, for example, in U.S. Pat. Nos. 4,937,385, 5,242,613, 5,250,737, EP 201197, WO 92/3524 and WO 92/397.

At the end of the reaction leading to the production of the raw polysulphide, the hydrogen sulphide contained in the raw product may be partly removed by degassing, in particular bubbling an inert gas (advantageously nitrogen, air or methane, etc.), vacuum evaporation or any other method known in the art.

c—Treatment According to the Invention of the Raw Polysulphide

According to the present invention, the raw polysulphide is treated with an alkylene carbonate in the presence of a basic catalyst and, optionally, a sulphur donor.

The alkylene carbonate used in the present invention may be ethylene carbonate, propylene carbonate, butylene carbonate or trimethylene carbonate, and more generally any compound of formula:

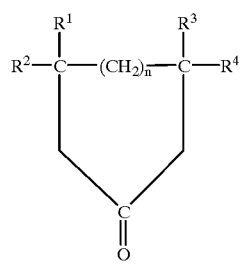

in which n is equal to 0, 1 or 2 and the symbols $R^1$, $R^2$, $R^3$ and $R^4$, which may be identical or different, each represent a hydrogen atom or an alkyl radical. The preferred alkylene carbonate is ethylene carbonate, a reactant which is inexpensive and not very toxic, its $LD_{50}$ (oral, rat) being equal to 10.4 g/kg.

The amount of alkylene carbonate to be used depends on the quantity of mercaptan(s) and hydrogen sulphide in the raw polysulphide. A mass ratio of alkylene carbonate relative to the raw polysulphide ranging from 0.001:1 to 0.2:1, and preferably 0.005:1 to 0.1:1 will generally be used.

Advantageously, if the quantity of mercaptan(s) and $H_2S$ remaining in the raw polysulphide is known, a molar ratio of alkylene carbonate relative to the sum of the molar quantities of mercaptan(s) and $H_2S$ will be used which is between 0.5:1 and 10:1, preferably between 0.9:1 and 2.5:1.

Non-limiting examples of basic catalysts usable in the process according to the invention which may be mentioned are:

amines (such as triethylamine or any other primary, secondary or tertiary amine), ammonium hydroxides, alkanolamines, mercaptides or alcoholates such as $R^5SNa$, $R^5ONa$, calcium or barium phenoxide, the compounds $R^5O(CH_2CH_2O)_mNa$, $R^5S(CH_2CH_2O)_mNa$ or a catalyst consisting of the combination of a mercaptan and an alkenoxide with an alkaline base (see Patent FR 2 607 496, the content of which is incorporated here by reference), $R^5$ denoting an alkyl or cycloalkyl radical and m an integer ranging from 1 to 15, metal hydroxides such as LIOH, NaOH and KOH, metal oxides or metal salts such as $Na_2O$, $K_2O$, MgO, $NaHCO_3$, $Na_2CO_3$ and $CaCO_3$), it being possible for these compounds to be used as they are or fixed on a support (for example an alumina or a silica), zeolites or hydrotalcites, aluminas, titanates, silicas or mixtures of these compounds, optionally modified by alkalis or alkaline-earth bases, basic anion-exchange resins such as, for example, resins based on styrene/divinylbenzene copolymer functionalized by primary, secondary or tertiary amine, quaternary ammonium, guanidine, amidine groups or a combination of these groups.

The catalyst may be used as it is or in the presence of a solvent such as water, an alcohol, carbon disulphide or any other solvent.

The basic catalyst of the present invention may already be contained in the raw polysulphide. This is the case, in particular, when the reaction by which the raw polysulphide is synthesized uses a basic catalyst which is not separated from the raw polysulphide. The basic catalyst of the present invention may also be added to the raw polysulphide.

The amount of basic catalyst may vary within wide limits. Generally, the catalyst is used in an amount ranging from 0.001%, to 50% relative to the weight of raw polysulphide, and preferably 0.05% at 25%.

Preferably, the basic catalyst used is the combination of a mercaptan and an alkene oxide with an alkaline base, or an anion-exchange resin. In the former case, the amount of catalyst is advantageously from 0.001 to 10% (preferably 0.05 to 2%) relative to the weight of raw polysulphide. When an anion-exchange resin is used, this amount is advantageously from 0.1 to 50% (preferably 1 to 25%) relative to the weight of raw polysulphide.

The process according to the invention may be carried out in any kind of suitable equipment. It is advantageously the equipment used for preparing the raw polysulphide. After the alkylene carbonate, and optionally the basic catalyst, has been added to the raw polysulphide (or vice versa), the mixture is stirred at a temperature of about 15 to 150° C. (preferably 50 to 120° C.) for a period of from 2 minutes to 10 hours (preferably from 5 minutes to 5 hours).

In certain cases (in particular for certain trisulphides such as di-t-dodecyl trisulphide or di-t-nonyl trisulphide) and if the alkylene carbonate on its own does not allow the residual mercaptan level to be reduced fast enough, it may be advantageous to use a certain amount of a sulphur donor in synergy with the alkylene carbonate.

The sulphur donor may be sulphur (in any form: liquid, bead, powder, etc.) or an organic polysulphide having 4 or more sulphur atoms per molecule. The preferred sulphur donors are sulphur, di-t-dodecyl pentasulphide and di-t-nonyl pentasulphide.

If the sulphur donor used is sulphur, a mass ratio of sulphur donor relative to the raw polysulphide of from 0:1 to 0.2:1 (preferably 0:1 to 0.1:1) will generally be used. If the sulphur donor used is an organic polysulphide, a mass ratio of sulphur donor relative to the raw polysulphide of from 0:1 to 1:1 (preferably 0:1 to 0.2:1) will generally be used.

The sulphur donor may be added before, at the same time as or even after the catalyst and the alkylene carbonate. Addition of the sulphur donor and alkylene carbonate simultaneously is preferred. The mixture is stirred at a temperature of about 15 to 150° C. (preferably 50 to 120° C.) for a period of from 2 minutes to 10 hours (preferably 5 minutes to 5 hours).

The finished product may then be purified if necessary. This can be done using the conventional separation methods such as distillation or filtration.

The process of this invention may also be adapted for continuous production.

As it has been described, the process of this invention has the effect of reducing the level of residual mercaptan and $H_2S$ to a level low enough for the polysulphide to be deodorized and stabilized.

EXAMPLES

The following examples illustrate the invention without limiting it. Unless otherwise indicated, the percentages given are percentages by mass.

Example 1
Preparation of di-t-dodecyl polysulphide having on average 5 sulphur atoms—finishing with ethylene carbonate by homogeneous catalysis 8.08 kg of t-dodecyl mercaptan and 60.6 g of a liquid catalyst obtained by reacting t-dodecyl mercaptan, ethylene oxide and sodium hydroxide according to the process described in Patent FR 2 607 496 were introduced into a 28 liter stainless steel reactor connected to a flare. 2.5 kg of solid sulphur were added over a period of one hour to the mixture which was heated to 90° C. and stirred continuously. Substantial release of $H_2S$ gas took place and, after 30 minutes, a strong flow of methane (200 l/h) was passed through the mixture for one and a half hours in order to remove the majority of the residual $H_2S$.

At the end of this operation, the raw polysulphide obtained contained 0.25% of mercaptan sulphur (determined by potentiometric titration using $AgNO_3$), which corresponds to 98% conversion of the initial mercaptan.

80 g of ethylene carbonate (corresponding to 1.2 mol equivalents relative to the residual mercaptan) was added to the same reactor in a single operation at 90° C. Significant release of gas took place. After one and a half hours of stirring at 90° C., the mixture was cooled and filtered to give 9.9 kg of finished product (more than 99% yield). Analysis of the finished product showed a mercaptan sulphur content of less than 10 ppm. The product was stable and did not contain $H_2S$, and no precipitate appeared after 3 months.

Example 2
Preparation of di-t-dodecyl polysulphide having on average 5 sulphur atoms—finishing with ethylene carbonate by heterogenous catalysis A mixture of 8.08 kg of t-dodecyl mercaptan and 808 g of Amberlyst® A21 ion-exchange resin (marketed by Röhm and Haas) was heated to 90° C. while being stirred in a 28 liter stainless steel reactor connected to a flare. 2.56 kg of sulphur in bead form were then introduced over a period of one hour. A substantial amount of $H_2S$ gas was released and was disposed of in the flare. After 30 minutes, a flow of methane (200 l/h) was passed through the mixture for two and a half hours, in order to remove the majority of the residual $H_2S$.

At the end of this operation, the raw polysulphide obtained contained 0.32% of mercaptan sulphur, which corresponds to 97.6% conversion of the mercaptan introduced.

A 50 g sample of this raw polysulphide taken without catalyst was introduced into a 100 ml three-necked flask fitted with a cooler. 5 g of Amberlyst® A21 resin and 0.52 g of ethylene carbonate (EC) were added thereto at 60° C. After stirring for two hours at this temperature, the mercaptan sulphur level was less than 10 ppm and the finished product did not contain $H_2S$. The product was stable over time (test 2 in Table 1).

Example 3
Comparative

The raw polysulphide (50 g) described in Example 2 was heated to 90° C. in the presence of A21 resin without ethylene carbonate. After 2 hours, the residual mercaptan sulphur level was 1200 ppm and was not stable (test 3 in Table 1).

The raw polysulphide (50 g) described in Example 2 was heated to 90° C. without resin in the presence of 0.52 g of ethylene carbonate. After 2 hours at 60 or 90° C., the residual mercaptan level was still 3200 ppm (test 4 in Table 1).

TABLE 1

Finishing of di-t-dodecyl polysulphide
(mercaptan sulphur level before reaction: 3200 ppm)

| Test | Resin catalyst | Reactant | mol ratio of reactant relative to residual mercaptan | Duration | Temperature | Mercaptan sulphur level after the reaction |
|---|---|---|---|---|---|---|
| 2 | A21 | EC | 1.5 | 2 h | 60° C. | 10 ppm |
| 3 | A21 | none | 0 | 2 h | 90° C. | 1200 ppm |
| 4 | none | EC | 1.5 | 2 h | 90° C. | 3200 ppm |

Example 4
Preparation of di-t-butyl trisulphide

A mixture of 135 g of t-butyl mercaptan (TBM) and 1.69 g of the liquid catalyst described in Example 1 was heated to 65° C. in a 500 ml glass reactor fitted with a cooler to 0° C. 43.5 g of solid sulphur were then added over a period of 35 minutes and under vigorous stirring. The stirring was continued at this temperature for 90 minutes, then the temperature was increased to 100° C. and nitrogen was passed through the reaction mixture with vigorous stirring for 120 minutes.

At this stage, the residual mercaptan sulphur level in the raw polysulphide was 1.27%, which corresponds to a TBM level of 3.5% by mass.

The raw polysulphide was then treated with 7.7 g of ethylene carbonate at 90° C. Substantial release of gas took place, and this ceased after 30 minutes. Nitrogen was then passed through the mixture with vigorous stirring. After 2 hours at 90° C., the product was filtered. A limpid, virtually odourless liquid was obtained which was stable over time and in which the residual mercaptan sulphur level was less than 15 ppm.

Example 5
Comparative

The raw polysulphide obtained in Example 4 was heated for two and a half hours at 90° C. under the same conditions as in Example 4, with nitrogen being passed through but without ethylene carbonate. The mercaptan sulphur level remained high (2600 ppm) and the product obtained had a foul smell.

Example 6
Preparation of di-t-dodecyl trisulphide 404 g of t-dodecyl mercaptan and 5 g of the liquid catalyst described in Example 1 were introduced into a 1 liter glass reactor. The mixture was heated to 110° C. and stirred continuously. 60.8 g of sulphur powder were then introduced over a period of 15 minutes. A substantial amount of $H_2S$ gas was released. After 20 minutes, a strong flow of nitrogen was passed through the mixture for one hour, in order to remove the majority of the $H_2S$.

After this operation, the raw polysulphide obtained contained 1.51% of mercaptan sulphur (determined by potentiometric titration using $AgNO_3$), corresponding to 90% conversion of the initial mercaptan.

19.5 g of ethylene carbonate (corresponding to 1.08 mol equivalents relative to the residual mercaptan) mixed with 9.6 g of sulphur powder were added to the same reactor in a single operation at 110° C. A significant amount of gas was released. After one and a half hours of stirring at 110° C., the mixture was cooled and filtered. Analysis of the finished product showed a mercaptan sulphur level of less than 9 ppm. The product was stable, did not contain $H_2S$ and no precipitate appeared after 3 months.

Example 7

Comparative

The raw polysulphide of the previous example was treated at 110° C. with 27.5 g of ethylene carbonate (corresponding to 1.5 mol equivalents relative to the residual mercaptan) without adding any sulphur donor. Very little gas was released.

After 10 hours of stirring at this temperature with appreciable nitrogen stripping, the residual mercaptan sulphur level was still more than 0.5% and the product was not stable.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Process for preparing a stabilized and deodorized organic polysulphide, comprising treating a raw organic polysulphide with an alkylene carbonate in the presence of a basic catalyst.

2. Process according to claim 1, wherein use is made of an alkylene carbonate of formula

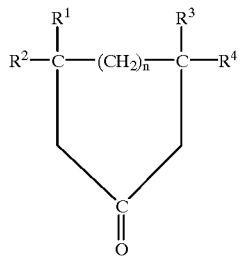

in which n is equal to 0, 1 or 2 and the symbols $R^1$, $R^2$, $R^3$, and $R^4$, which are identical or different, each represent a hydrogen atom or an alkyl radical.

3. Process according to claim 1, wherein the alkylene carbonate is ethylene carbonate.

4. Process according to claim 1, wherein the mass ratio of the alkylene carbonate to the raw polysulphide is between 0.001:1 and 0.2:1.

5. Process according to claim 1, wherein the molar ratio of the alkylene carbonate to the sum of the molar quantities of mercaptan(s) and hydrogen sulphide present in the raw polysulphide is between 0.5:1 and 10:1.

6. Process according to claim 1, wherein the basic catalyst is used in an amount ranging from 0.001 to 50% relative to the weight of raw polysulphide.

7. Process according to claim 1, wherein the basic catalyst consists of the combination of a mercaptan and an alkene oxide with an alkaline base.

8. Process according to claim 7, wherein the catalyst is used in an amount ranging from 0.001 to 10% relative to the weight of raw polysulphide.

9. Process according to claim 1, wherein the basic catalyst is an anion-exchange resin.

10. Process according to claim 1, wherein the catalyst is used in an amount ranging from 0.1 to 50% relative to the weight of raw polysulphide.

11. Process according to claim 1, wherein the treatment is carried out at a temperature ranging from about 15 to 150° C.

12. Process according to claim 1, wherein the duration of the treatment is between 2 minutes and 10 hours.

13. Process according to claim 1, wherein the treatment is also carried out in the presence of a sulphur donor.

14. Process according to claim 13, wherein the sulphur donor used is sulphur or an organic polysulphide having at least 4 sulphur atoms per molecule.

15. Process according to claim 14, wherein the sulphur donor is sulphur used in a mass ratio of the sulphur to the raw polysulphide ranging from 0:1 to 0.2:1.

16. Process according to claim 14, wherein the sulphur donor is an organic polysulphide, used in a sulphur donor/raw polysulphide mass ratio ranging from 0:1 to 1:1.

17. Method comprising treating raw polysulphide $RS_nR'$ in which the symbols R and R' denote alkyl radicals having 4 to 12 carbon atoms and n is a number ranging from 3 to 6 according to the process of claim 1.

18. Method comprising preparing tert-butyl, tert-nonyl or tert-dodecyl polysulphide, or tert-butyl trisulphide according to the process of claim 3.

19. Method comprising preparing tert-dodecyl trisulphide according to the process of claim 13.

20. Process according to claim 4, wherein the mass ratio is between 0.005:1 and 0.1:1.

21. Process according to claim 5, wherein the molar ratio is between 0.9:1 and 2.5:1.

22. Process according to claim 6, wherein the amount is from 0.05 to 25%.

23. Process according to claim 8, wherein the amount is from 0.05 to 2%.

24. Process according to claim 10, wherein the amount is from 1 to 25%.

25. Process according to claim 11, wherein the temperature is 50 to 120° C.

26. Process according to claim 12, wherein the duration is between 5 minutes and 5 hours.

27. Process according to claim 15, wherein the mass ratio is from 0:1 to 0.1:1.

28. Process according to claim 16, wherein the sulphur donor is di-t-dodecyl or di-t-nonyl pentasulphide and the mass ratio is from 0:1 to 0.2:1.

* * * * *

UNITED STATES PATENT AND TRADEMARK OFFICE
CERTIFICATE OF CORRECTION

PATENT NO. : 6,114,586
DATED : September 5, 2000
INVENTOR(S) : Devaux et al.

It is certified that error appears in the above-identified patent and that said Letters Patent is hereby corrected as shown below:

Title page,
References to [56] References Cited U.S. PATENT DOCUMENTS

| | | |
|---|---|---|
| 5,218,147 | 06/93 | Shaw |
| 5,403,961 | 04/95 | Shaw |
| 4,876,389 | 10/89 | Gongora et al. (corresponds to FR 2 607 496) |
| 5,068,445 | 11/91 | Arretz (corresponds to EP 337 837) |
| 5,155,275 | 10/92 | Shaw |
| 5,206,439 | 04/93 | Shaw |
| 5,530,163 | 06/96 | Shaw |
| 2,237,625 | 04/41 | Olin |
| 3,022,351 | 02/62 | Mihm et al. |
| 3,038,013 | 06/62 | Warner |
| 4,564,709 | 01/86 | Koyama et al. |
| 4,937,385 | 06/90 | Buchholz et al. |
| 5,242,613 | 09/93 | Ozbalik et al. |
| 5,250,737 | 10/92 | Oabalik |
| 3,392,201 | 07/68 | Warner |
| 3,595,820 | 07/71 | Herder et al. |

UNITED STATES PATENT AND TRADEMARK OFFICE
CERTIFICATE OF CORRECTION

PATENT NO. : 6,114,586
DATED : September 5, 2000
INVENTOR(S) : Devaux et al.

It is certified that error appears in the above-identified patent and that said Letters Patent is hereby corrected as shown below:

Insert the following references to [56] References Cited FOREIGN PATENT DOCUMENTS

| | | |
|---|---|---|
| FR 2 607 496 | 06/88 | France (corresponds to US 4,876,389) |
| EP 337,837 | 10/89 | Europe (corresponds to US 5,068,445) |
| JP 58-140063 | 08/83 | Japan |
| FR 1 381 625 | 11/64 | France |
| WO 97/21649 | 06/97 | WIPO |
| WO 97/21673 | 06/97 | WIPO |
| EP 201 197 | 07/90 | EPO |
| WO 92/03524 | 03/92 | WIPO |
| WO 92/00397 | 01/92 | WIPO |
| EP 025 944 | 04/81 | EPO |
| FR 2 635 775 | 03/90 | France |
| FR 1 553 249 | 01/69 | France |

Signed and Sealed this

Thirtieth Day of October, 2001

Attest:

NICHOLAS P. GODICI
Attesting Officer  Acting Director of the United States Patent and Trademark Office